(12) United States Patent
Rutkowski et al.

(10) Patent No.: US 8,436,844 B2
(45) Date of Patent: May 7, 2013

(54) BI-STABLE DISPLAY FAIL SAFES AND DEVICES INCORPORATING THE SAME

(75) Inventors: Paul S. Rutkowski, Carmel, IN (US);
Randy J. Gardner, Bloomington, IN (US); Michael J. Blackburn, Indianapolis, IN (US); Michel A. Cadio, Carmel, IN (US); Robert G. Davies, Carmel, IN (US); James R. Kurtock, Carmel, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 715 days.

(21) Appl. No.: 12/486,805

(22) Filed: Jun. 18, 2009

(65) Prior Publication Data

US 2010/0323431 A1 Dec. 23, 2010

(51) Int. Cl.
*G06F 3/038* (2006.01)
*G09G 5/00* (2006.01)

(52) U.S. Cl.
USPC .......................................................... 345/211

(58) Field of Classification Search .................. 345/211
See application file for complete search history.

(56) References Cited

U.S. PATENT DOCUMENTS

| | | | |
|---|---|---|---|
| 4,173,756 A * | 11/1979 | Kawagai et al. | 340/636.15 |
| 4,247,852 A * | 1/1981 | Utzinger | 345/618 |
| 6,462,859 B1 | 10/2002 | Bastiaens et al. | |
| 6,476,796 B1 | 11/2002 | Kuzunuki et al. | |
| 6,906,779 B2 | 6/2005 | Chan-Park et al. | |
| 6,972,893 B2 | 12/2005 | Chen et al. | |
| 7,144,942 B2 | 12/2006 | Zang et al. | |
| 7,177,066 B2 * | 2/2007 | Chung et al. | 359/296 |
| 7,243,261 B2 * | 7/2007 | Yashiro | 714/14 |
| 2005/0083284 A1 | 4/2005 | Huang et al. | |
| 2006/0009238 A1 | 1/2006 | Stanco et al. | |
| 2006/0017659 A1 | 1/2006 | Ogawa et al. | |
| 2007/0040825 A1 * | 2/2007 | Mamba et al. | 345/211 |
| 2007/0164975 A1 | 7/2007 | Lim et al. | |
| 2008/0273007 A1 | 11/2008 | Ng et al. | |

FOREIGN PATENT DOCUMENTS

| | | |
|---|---|---|
| EP | 1 624 439 A2 | 2/2006 |
| EP | 1 783 536 A1 | 5/2007 |
| EP | 1 887 544 A1 | 2/2008 |
| GB | 2 080 593 A | 7/1981 |

OTHER PUBLICATIONS

Walt Kester, Analog-Digital Conversion (Chapter 2)—Analog Devices Mar. 2004.*
Dialog Semiconductor Data Sheet, DA8523 Cascadable 192-output EDP Driver, Document Ref. DA8523-DS1c, www.dialog-semiconductor.com, pp. 1-19, Version 1c.

* cited by examiner

*Primary Examiner* — Alexander S Beck
*Assistant Examiner* — Joseph Pena
(74) *Attorney, Agent, or Firm* — Dinsmore & Shohl LLP

(57) ABSTRACT

A control circuit and method for controlling a bi-stable display having bi-stable segments each capable of transitioning between an on state and an off state via application of a voltage are disclosed. The voltage is provided to a display driver from a charge pump, and supplied to individual ones of the bi-stable segments via outputs from the display driver in accordance with display instructions provided by a system controller. Both a bi-stable segment voltage level of at least one of the outputs of the display driver and a charge pump voltage level of the voltage are detected and compared to a valid bi-stable segment voltage level and a valid charge pump voltage level, respectively. A malfunction signal may be provided to the system controller if either of the detected voltage levels is not valid. The control circuit is useful in an electronic device such as, for example, a blood glucose measuring device.

45 Claims, 8 Drawing Sheets

BI-STABLE DISPLAY FAIL SAFES AND DEVICES INCORPORATING THE SAME

TECHNICAL FIELD

The present invention relates generally to bi-stable displays and, more particularly, bi-stable display fail safes and devices incorporating bi-stable displays.

BACKGROUND

Bi-stable displays such as electronic paper are an attractive choice for a user interface because they are more flexible, thinner and more robust than other similar displays such as LCD displays. Bi-stable displays consume relatively little power because they only require power to update the contents of the display. The display retains text and images indefinitely without power until a display driver updates the display by applying an electric field across segment electrodes of particular segments. Further, bi-stable displays may provide a user interface with a wider viewing angle and higher contrast than other conventional displays.

However, because bi-stable displays have the ability to display information without any power consumption, bi-stable displays may also display unwanted information to the user in the event of an internal device failure. It may be important in many applications that correct and updated information be displayed on the bi-stable display. For example, if a display driver within a device incorporating a bi-stable display were to malfunction and not provide appropriate voltages to the segments of the bi-stable display, the display would continue to display information previously written to the display. This may cause misleading information to be provided to the user of the device.

SUMMARY

In one embodiment, a control circuit for controlling a bi-stable display includes a system controller, a display driver, a bi-stable segment monitoring module, and a charge pump. The charge pump generates one or more charge pump voltages for driving the bi-stable display. The bi-stable display may include a plurality of bi-stable segments capable of transitioning between an on state and an off state with the application of the charge pump voltages. The display driver has a plurality of outputs that correspond to the plurality of bi-stable segments, and may be operable to control the bi-stable segments by applying the charge pump voltages to the plurality of bi-stable segments in accordance with display instructions provided by the system controller. The bi-stable segment monitoring module may be operable to detect a bi-stable segment voltage level of at least one output of the display driver and compare the detected bi-stable segment voltage level of the output with a valid bi-stable segment voltage level of the output.

In another embodiment, a blood glucose measuring device for measuring a blood glucose level of a blood sample provided on a disposable measurement strip is provided. The blood glucose measuring device includes a system controller, a bi-stable display, and a bi-stable control circuit. The bi-stable display may include a plurality of bi-stable segments capable of transitioning between an on state and an off state with the application of charge pump voltages. The bi-stable control circuit includes a charge pump, a display driver, a bi-stable segment monitoring module, and a charge pump monitoring module. The charge pump generates one or more charge pump voltages. The display driver may include a plurality of outputs that correspond to the bi-stable segments, and controls the bi-stable segments by applying the charge pump voltages in accordance with display instructions provided by the system controller. The bi-stable segment monitoring module detects a bi-stable segment voltage level of at least one output of the display driver and compares the detected bi-stable segment voltage level of the output with a valid bi-stable segment voltage level of the output. The charge pump monitoring module monitors a charge pump voltage level of the charge pump and compares the monitored charge pump voltage level with a valid charge pump voltage level. The system controller is configured to measure the blood glucose level of the blood sample and provide display instructions corresponding at least in part to the blood glucose measurement to the display driver.

In another embodiment, an electronic device includes a system controller, a charge pump, a bi-stable display, and a display driver. The charge pump generates one or more charge pump voltages. The bi-stable display includes one or more characters capable of displaying an intended character value, each character comprising one or more first bi-stable segments and one or more second bi-stable segments. Each second bi-stable segment includes a plurality of sub-segments. The display driver includes a plurality of outputs that correspond to the first bi-stable segments and the sub-segments, and is operable apply the charge pump voltages to the first bi-stable segments and the sub-segments via the plurality of outputs in accordance with display instructions provided by the system controller.

In yet another embodiment, a method for controlling a bi-stable display having a plurality of bi-stable segments each capable of transitioning between an on state and an off state via application of a voltage is provided. The method includes providing the voltage from a charge pump to individual ones of the plurality of bi-stable segments via a plurality of outputs from the display driver in accordance with display instructions provided by a system controller. The method further includes detecting both a bi-stable segment voltage level of at least one of the plurality of outputs of the display driver and a charge pump voltage level of the voltage and comparing both the detected bi-stable segment voltage level with a valid bi-stable segment voltage level and the detected charge pump voltage level with a valid charge pump voltage level. A malfunction signal may be provided to the system controller if either the detected bi-stable segment voltage level is not equal to the valid bi-stable segment voltage level, or the charge pump voltage level is not within a tolerance range of the valid charge pump voltage level.

In yet another embodiment, a control circuit for controlling a bi-stable display includes a system controller, a display driver, a charge pump, and a charge pump monitoring module. The charge pump generates one or more charge pump voltages for driving the bi-stable display. The bi-stable display may include a plurality of bi-stable segments capable of transitioning between an on state and an off state with the application of the charge pump voltages. The display driver has a plurality of outputs that correspond to the plurality of bi-stable segments, and may be operable to control the bi-stable segments by applying the charge pump voltages to the plurality of bi-stable segments in accordance with display instructions provided by the system controller. The charge pump monitoring module monitors a charge pump voltage level of the charge pump, compares the monitored charge pump voltage level with a valid charge pump voltage level, and provides a charge pump malfunction signal to the system controller if the monitored charge pump voltage level is not within a tolerance range of the valid charge pump voltage level.

These and other advantages and features of the invention disclosed herein, will be made more apparent from the description, drawings and claims that follow.

BRIEF DESCRIPTION OF THE DRAWINGS

The following detailed description of the embodiments of the present invention can be best understood when read in conjunction with the following drawings, where like structure is indicated with like reference numerals, and in which.

DETAILED DESCRIPTION

Figure 1:
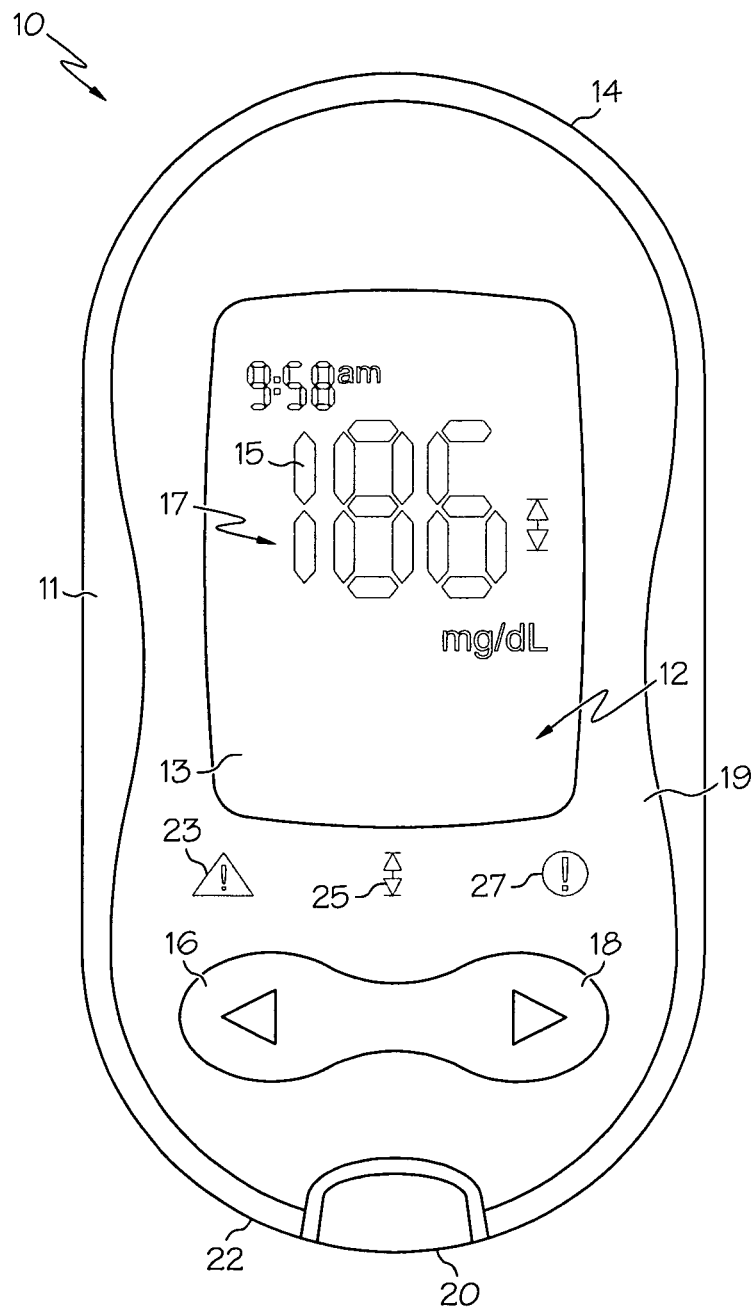
FIG. 1 depicts a front view of an embodiment of a medical diagnostic device having a bi-stable display according to one or more embodiments.

Referring to the drawings, embodiments described herein relate generally to bi-stable display fail safes and portable handheld devices that incorporate a bi-stable display. For example, a bi-stable display may be incorporated into a handheld medical diagnostic device, such as a blood glucose monitor. The bi-stable display may be used to provide a user with relevant information. Although embodiments of the fail safes may be described herein in the context of medical diagnostic devices, embodiments are not limited thereto. The fail safes may be incorporated into any device wherein information provided on a bi-stable display should be correct and undesirable bi-stable display errors are to be avoided.

Embodiments of the present disclosure may provide bi-stable fail safes to prevent misleading information from being displayed on the bi-stable display. Embodiments may monitor bi-stable segment voltage levels, charge pump voltage levels and power levels of a power source to determine whether the device is operating correctly. If an error is detected, appropriate action may be taken, such as sounding an alarm, generating an error message or locking out the device. Other fail safe embodiments may protect against bi-stable display errors by further segmenting main bi-stable segments of a bi-stable character into smaller sub-segments to prevent the failure of an entire bi-stable segment. Exemplary bi-stable fail safes and devices incorporating a bi-stable display will be described in detail below.

Referring to FIG. 1, an exemplary portable, handheld medical diagnostic device 10 with a display device 12 behind a transparent, protective lens 13 includes a protective enclosure 14 that protects electronics therein. In the illustrated embodiment, the display device 12 includes a bi-stable display such as an electrophoretic display, which may be an information display that forms visible images by rearranging charged particles using an electric field. The display device 12 is used for electrophoretically displaying graphics, text, and other elements to a user. The display device 12 may be any suitable bi-stable display device. The protective enclosure 14 of the exemplary embodiment is somewhat oval in shape with an outer frame portion 11 and an hourglass-shaped inner portion 19 bounded by the frame portion 11. Any other suitable shapes may be used for the protective enclosure 14, frame portion 11 and inner portion 19, such as rectangular shapes, circular shapes, etc. Further, display device 12 may comprise any other variety of indicators, including, but not limited to a series of lights and/or other types of light devices as opposed to a single integrated display screen. In some embodiments, the display device 12 may comprise a touch-screen user interface that is used with the tip of a finger of the user and/or a stylus or other touching device to select elements from the screen, to draw figures, and to enter text with a character recognition program running on the device 10. In some embodiments, the medical diagnostic device 10 may also include other types of output devices such as for example, sound devices, vibration devices, etc.

The medical diagnostic device 10 further includes a user interface, which may include buttons 16 and 18. The buttons 16 and 18 are illustrated as right and left arrow buttons, but may be of any other suitable configuration. The buttons 16 and 18 may be used by an operator, for example, to view memory of the medical diagnostic device 10, adjust settings of the device and scroll through test results. The buttons 16 and 18 may be manually actuated, such as by pressing the buttons. In the illustrated embodiment, the buttons 16 and 18 comprise touch sensors (e.g., capacitive touch sensors) that can be actuated by placing a tip of the finger within the button areas. In this embodiment, the buttons 16 and 18 may not move. Instead, the buttons 16 and 18 may be indicated visually to identify where to place the finger. In other embodiments utilizing touch sensors, the buttons 16 and 18 may move, for example, to bring the finger or touching device into close proximity to the touch sensor. In some embodiments, the medical diagnostic device 10 may provide other button or input types such as an OK button and/or joy stick/track ball, which a user may utilize to navigate through a software drive menu provided on the display device 12. Additional buttons (e.g., 23, 25 and 27) may be used as shortcut buttons, for example, to call up a certain program on the medical diagnostic device 10, as a method of scrolling, to select items from a list, or to provide any function that the software designer of the device may assign to the button or set of buttons. Each button size, layout, location, and function may vary for each manufacturer and model of the medical diagnostic device 10.

A test strip port 20 may be located at a bottom end 22 of the medical diagnostic device 10. The test strip port 20 may be sized to receive a test strip (not shown) for testing a blood sample. In one embodiment, the medical diagnostic device 10 is an in vitro diagnostic device that is used to test blood and other body fluids and tissues to obtain information for the diagnosis, prevention and treatment of a disease. The medical diagnostic device 10 may be a self-testing blood glucose meter for people with diabetes. In one embodiment, the medical diagnostic device 10 is a handheld reagent-based blood glucose meter, which measures glucose concentration by observing some aspect of a chemical reaction between a reagent and the glucose in a fluid sample. The reagent may be a chemical compound that is known to react with glucose in a predictable manner, enabling the monitor to determine the concentration of glucose in the sample. For example, the medical diagnostic device 10 may be configured to measure a voltage or a current generated by the reaction between the glucose and the reagent.

Figure 2:
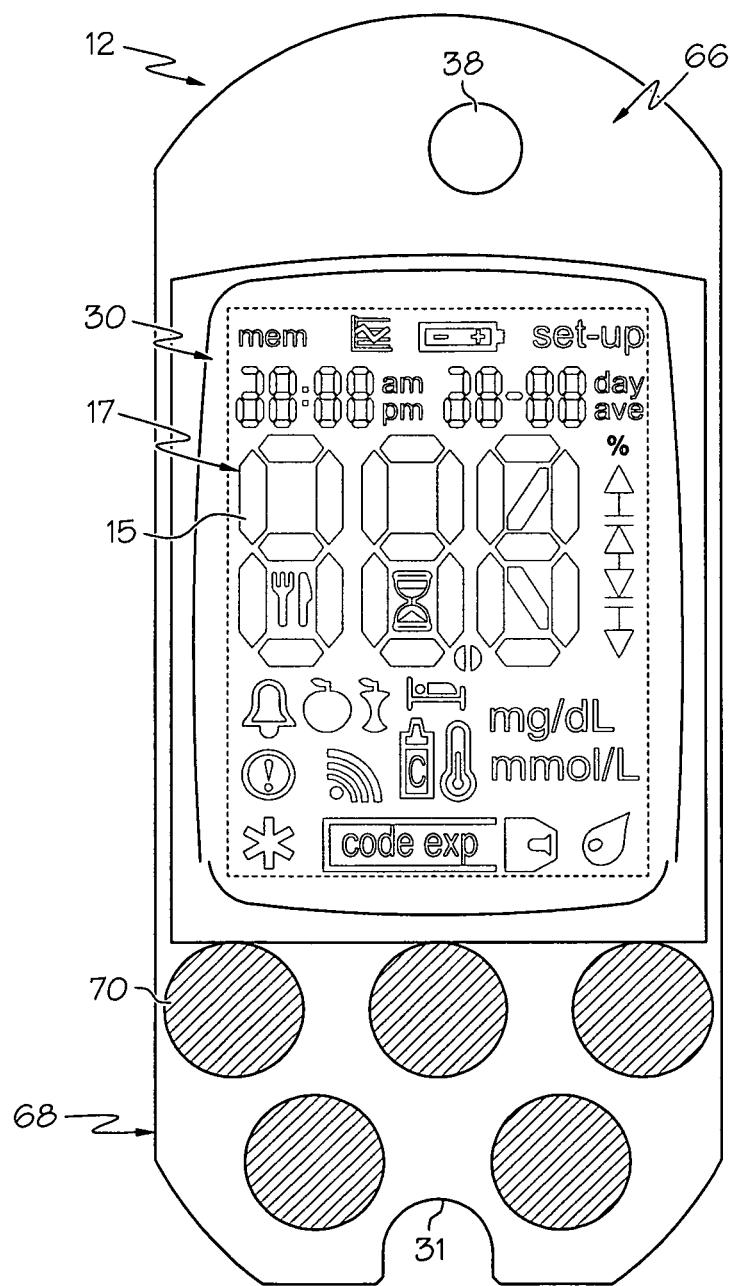
FIG. 2 depicts a front view of an embodiment of a bi-stable display component and a touch screen component according to one or more embodiments.
Figure 3:
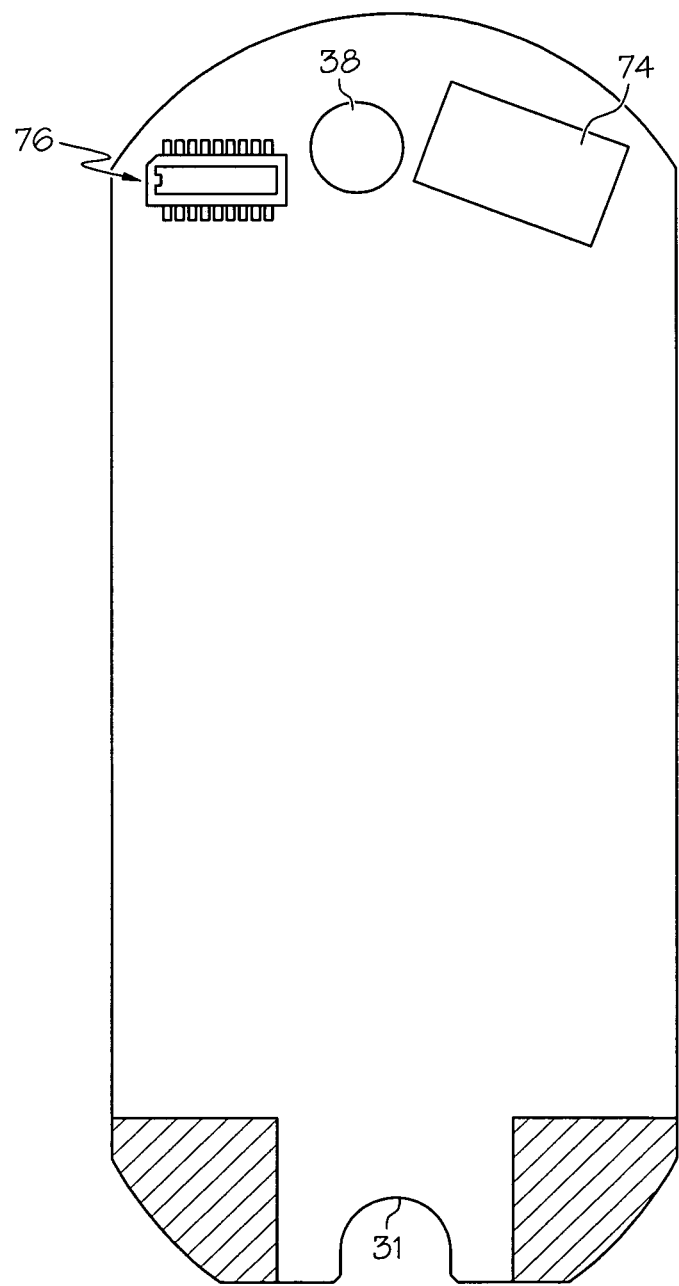
FIG. 3 depicts a rear view of an embodiment of a bi-stable display component and a touch screen component according to one or more embodiments.

FIGS. 2 and 3 illustrate an exemplary display device 12 that includes a bi-stable display component 66 and a touch sensor component 68. The display device 12 may be made of a flexible substrate. The touch sensor component 68 includes touch sensor pads 70 indicated by circular areas on the touch sensor component 68, which may be aligned with the buttons 16 and 18. Other shapes for the touch sensor pads 70 may be used. In the illustrated embodiment, the bi-stable display component 66 comprises a visible area 30 that is located under the protective lens 13 when the medical diagnostic device is fully assembled. Within the visible area 30 are a plurality of characters 17 made up of bi-stable segments 15. The characters 17 may be alpha-numerical characters, or symbols (e.g., a battery or a thermometer symbol). The characters 17 provide information to the medical diagnostic device user, such as a blood glucose test result, an insulin reminder, date/time, low battery and other information as illustrated in FIG. 3.

Each bi-stable segment of the bi-stable display component 66 comprises a top electrode and a bottom electrode (not shown). The top electrode is transparent to allow ambient light to pass through. Between the top and bottom electrodes is a layer containing colored oil (e.g., black oil) that suspends white particles having a particular charge. To control the bi-stable segment, a voltage may be applied across the top and bottom electrodes. The charged particles will migrate toward the electrode having the charge that is opposite to the charge of the particles. When the particles are located near the top electrode (e.g., the particles are negatively charged and a positive voltage is or was recently present at the top electrode), the bi-stable segment will appear white or "off" because ambient light reflects off of the particles. Conversely, when the particles are located near the bottom electrode (e.g., the particles are negatively charged and a positive voltage is or was recently present at the bottom electrode), ambient light is absorbed by the colored oil, making the bi-stable segment appear dark or "on." Because the display is bi-stable, the bi-stable segment remains in its present state until a voltage having a reverse polarity is applied to the top and bottom electrodes. It will be understood that other bi-stable display configurations may be utilized, such as bi-stable displays that use black and white ink, or rotating balls having a first color on one side and a second color on the opposite side, for example.

As described below, to individually control each bi-stable segment of the display, a display driver 74 (FIG. 3) may apply charge pump voltages to the top and bottom electrodes and reverse the voltage polarity to turn the bi-stable segments on and off. Conductive traces run from the outputs of the display driver 74 to the electrodes of the bi-stable segments 15 within the visible area 30. The display driver 74 may be used to integrate functions needed for driving the bi-stable display component 66. Data may be clocked into the device using a serial peripheral interface ("SPI") before integrated charge pumps within the display driver 74 (or external charge pumps) generate the voltages required to drive the display. Once the display has been updated, the display driver 74 can be switched into standby or power down mode while still retaining the image on the display. The display device 12 includes a connector 76 on the rear side (FIG. 3) configured to connect the display device 12 to a main circuit board (not shown), which may include components such as a system controller, power sources such as batteries and super capacitors, or other components (see FIGS. 7 and 8). The system controller (e.g., system controller 102, FIG. 7) may send display instructions to the display driver 74 (e.g., display results of most recent blood glucose measurement test). The display driver 74 and touch sensor component 68 may also send data and signals to the system controller through the connector 76.

Figure 4:
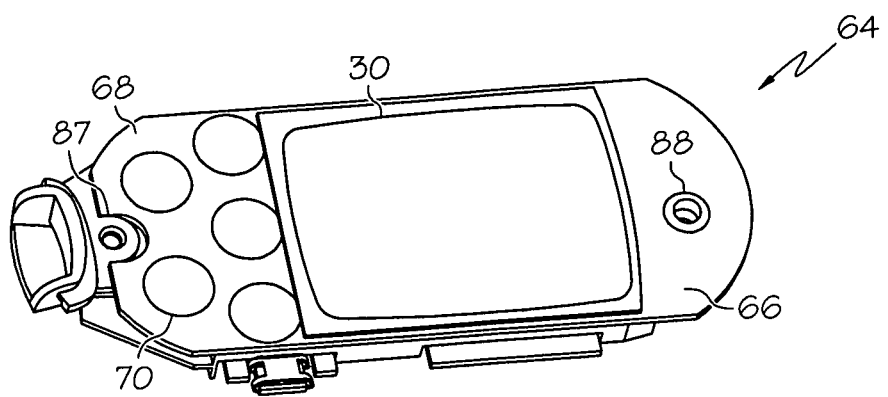
FIG. 4 depicts a diagrammatic perspective front view of an embodiment of a frame for supporting components of the medical diagnostic device of FIG. 1 according to one or more embodiments.
Figure 5:
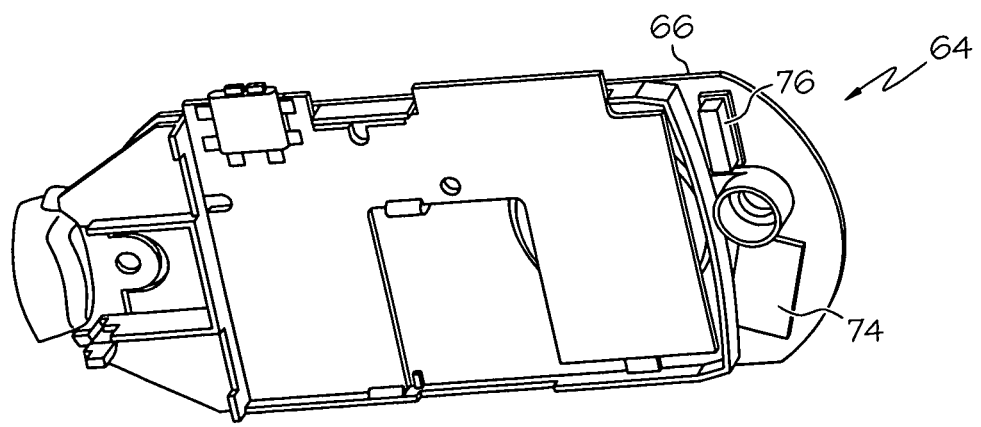
FIG. 5 depicts a diagrammatic perspective rear view of an embodiment of a frame for supporting components of the medical diagnostic device of FIG. 1 according to one or more embodiments.
Figure 6:
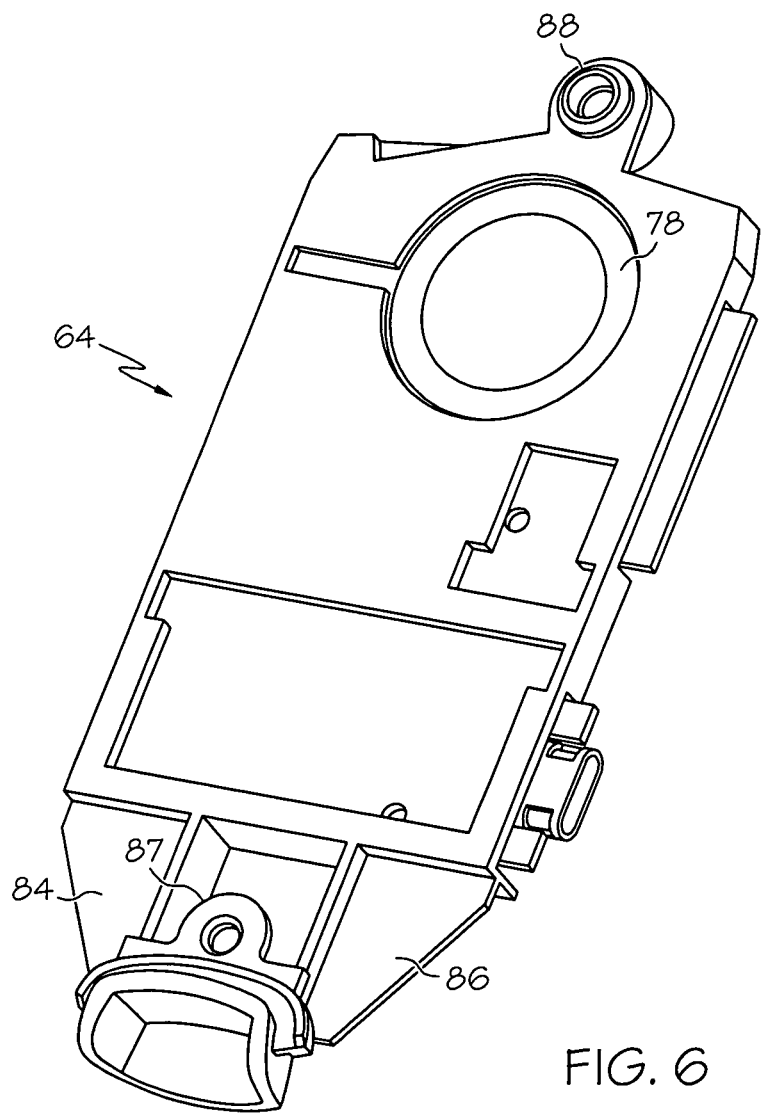
FIG. 6 depicts a diagrammatic perspective top view of the frame of FIG. 1 with components removed according to one or more embodiments.

FIGS. 4-6 illustrate an exemplary frame assembly 64 suitable for use with the medical diagnostic device 10. The frame assembly 64 is configured to fit within the protective enclosure 14 and couple the display device 12 to other components such as a main circuit board. FIG. 4 is a top perspective view of a frame assembly 64 having a display device 12 disposed therein, FIG. 5 is a bottom perspective view of the frame assembly (with a display device 12 disposed therein) and in FIG. 6, the frame assembly 64 is shown with the electronic paper component 66 and touch sensor component 68 removed. The frame assembly 64 is configured to accept the display device 12. In the illustrated embodiment, the display device 12 is coupled to the frame assembly by recesses 38 and 31 and corresponding boss members 88 and 87. Referring to FIG. 6, an audio component 78, such as a buzzer, is carried by the frame assembly 64, beneath the electronic paper component 66. Insets 84 and 86 are provided to allow mounting of the controller devices and other components for the touch sensor component 68.

Figure 7:
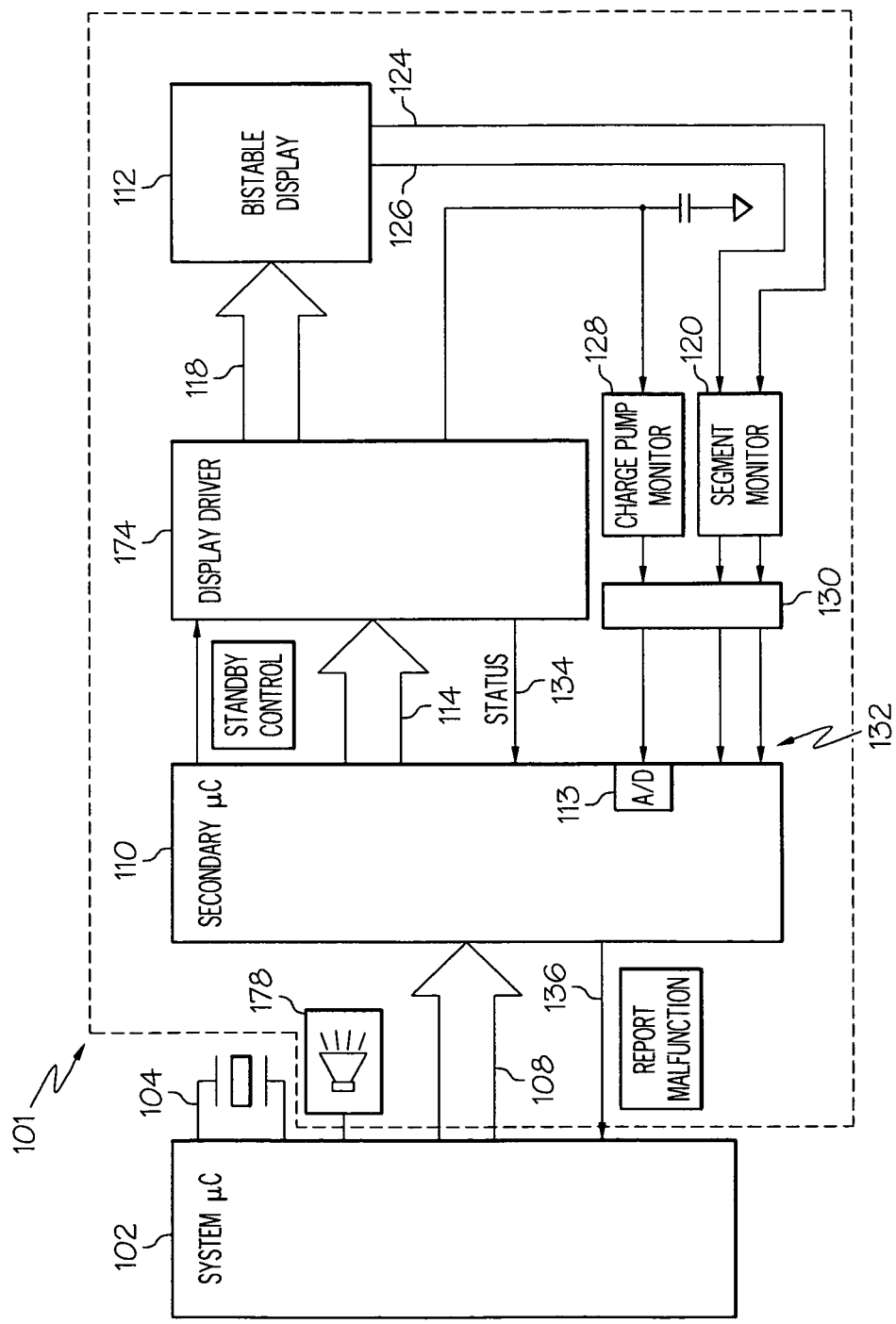
FIG. 7 depicts a schematic diagram of exemplary bi-stable display circuitry for detecting bi-stable segment and charge pump errors according to one or more embodiments.

Referring now to FIG. 7, an exemplary bi-stable display control and error detection circuit ("display circuitry") 101 for detecting bi-stable segment and charge pump failures will now be described. Generally, the display circuitry comprises 101 a secondary controller 110, a display driver 174, a charge pump monitoring module 128 and a bi-stable segment monitoring module 120. The charge pump monitoring module 128 and the bi-stable segment monitoring module 120 may comprise dedicated hardware or may be purely software. In other embodiments, the charge pump monitoring module 128 and the bi-stable segment monitoring module 120 may be a combination of both hardware and software. The display driver 174 may include a charge pump that generates the requisite voltages from a logic voltage level to drive the bi-stable display, or charge pump circuitry separately from the display driver 174 may be provided. Although the illustrated embodiment includes a secondary controller 110, in other embodiments the functionality of the secondary controller 110 may be provided in the display driver 174 or the system controller 102.

The system controller 102 is configured to communicate with bi-stable control and error detection circuitry by way of any communication protocol. The system controller 102 may, along with other electronic components, perform diagnostic measurements such as the blood glucose measurement described above. The system controller 102 may then provide the secondary controller 110 with display instructions that correspond with a desired output to display in the visible area 30 of the display device 112. The secondary controller may then pass the display instructions to the display driver 174, or it may perform signal processing and then provide the display instructions to the display driver 174. In other embodiments, the system controller 102 may provide the display instructions directly to the display driver 174.

The display driver 174, which is electrically coupled to the bi-stable segments of the bi-stable display via conductive traces (illustrated by symbol 118) running from outputs of the display driver 174 to the bi-stable segment electrodes, is configured to receive the display instructions and apply appropriate charge pump voltages to the bi-stable segment electrodes via the display driver outputs. For example, the bi-stable segments may be switched from an "on" state to an "off" state by reversing the polarity of the voltage on the bi-stable segment electrodes.

It may be important to provide bi-stable display fail safes in a medical diagnostic device 10 so that a user does not receive misinformation regarding his or her medical condition. A bi-stable segment failure resulting from a malfunctioning display driver 174 output, a broken conductor from a display driver output to the bi-stable segment electrodes or other similar faults may lead to providing misleading information to the user of the device. For example, if bi-stable segment "A" does not transition to an "on" state (black), an intended display of "700" may appear as a "100," thereby potentially misleading the user. Therefore, it may be desirable to monitor some or all of the bi-stable segments and alert the user to any fault conditions that may be present.

The bi-stable segment monitoring module 120 is configured to monitor bi-stable segment voltage levels directly at the electrodes of the bi-stable segments on the display device 12. If a bi-stable segment is detected as malfunctioning, a bi-stable segment malfunction signal may be provided to the system controller 102 which may take appropriate action, such as initiating a buzzer or speaker 178. In the illustrated embodiment, each bi-stable segment has two monitoring traces extending therefrom. A first trace (e.g., trace 124) extends from the top electrode and a second trace (e.g., trace 126) originates from the bottom electrode. These traces may provide the bi-stable segment monitoring module 120 with the voltages that are at the top and bottom electrodes of each bi-stable segment. In this manner, the bi-stable segment monitoring module 120 may monitor the true voltages of the electrodes directly at the bi-stable segment electrodes.

Figure 9:
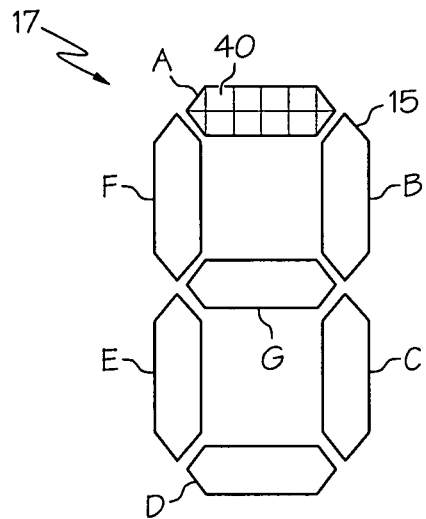
FIG. 9 depicts a diagrammatic illustration of an exemplary seven segment character according to one or more embodiments.

The bi-stable segment monitoring module 120 is configured to measure the voltage of the top and bottom electrodes of some or all of the bi-stable segments 15 in the visible area 30 of the display device 112 to test the outputs of the display driver 174. In some embodiments, only critical bi-stable segments of characters 17 may be monitored, such as bi-stable segment A as illustrated in FIG. 9. The bi-stable segment monitoring module 120 determines the voltage level state at the bi-stable segments, which may be a positive polarity state (i.e., the top electrode is at a voltage potential that is greater than the bottom electrode), a common state (i.e., the top electrode and bottom electrode have the same voltage potential), or a negative polarity state (i.e., the top electrode is at a voltage potential that is lower than the bottom electrode). Therefore, the bi-stable segment monitoring module 120 may be operable to determine the voltage differential of the voltages provided on the traces extending directly from the bi-stable segments, which may be accomplished by the use of operational amplifiers or other logic gates and integrated circuits known in the art to detect voltage levels. In the illustrated embodiment, the output voltages received on the bi-stable segment traces (e.g., 124 and 126) are lowered from the relatively high drive voltages to a logic voltage level by the level translation module 130, which may be a DC to DC converter. The level translation module may be provided before or after the bi-stable segment monitoring module 120.

The bi-stable segment monitoring module 120 and the level translation module 130 cooperate to provide the secondary controller 110 with signals that indicate the voltage levels at each of the monitored bi-stable segments (see secondary controller inputs 132) or the voltage polarity of the top and bottom electrodes. The secondary controller 110 may compare the detected bi-stable segment voltage levels with valid bi-stable segment differential voltage levels to determine if a bi-stable segment did not update properly. The valid bi-stable segment differential voltage level corresponds to the voltage level that a particular electrode of a particular bi-stable segment should have been as provided by the display instructions received from the system controller 102. Based on the display instructions, the secondary controller 110 is programmed to know what the voltage level (or voltage differential) should be at each of the bi-stable segments monitored by the bi-stable segment monitoring module 120 (i.e., the valid bi-stable segment voltages). These valid bi-stable segment voltage levels or valid differential voltage levels may be updated in a memory location of the secondary controller 110 (or another memory device) each time the secondary controller receives new display instructions. For example, a valid bi-stable segment voltage may be 15 volts for the top electrode and 30 volts for the bottom electrode to turn the particular b-stable segment on or off. If the detected bi-stable segment voltage level for a bi-stable segment does not match a corresponding valid bi-stable segment voltage level, or if a detected bi-stable segment voltage differential does not match a valid bi-stable segment voltage differential, the bi-stable segment monitoring module (or the secondary controller 110) may provide a bi-stable segment malfunction signal to the system controller 102 (136).

For example, if the top electrode of a particular bi-stable segment should have been at a positive voltage level with respect to the bottom electrode, and the detected bi-stable segment voltage signal indicates a common or negative voltage level with respect to the bottom electrode, the bi-stable segment may not have updated properly and a bi-stable segment malfunction signal may be provided to the system controller 102. The system controller 102 may then take appropriate action to warn the user that the display device 12 may not be operating properly, such as initiating a buzzer or speaker 178. In other embodiments, the secondary controller 110 or the bi-stable segment monitoring module 120 may directly issue an alarm via a buzzer or speaker without first notifying the system controller 102. In certain situations, such as the occurrence of a severe error, the medical diagnostic device 10 may be disabled from further use. Other embodiments may attempt to re-write the bi-stable segment or segments 15 first before issuing an alarm to determine whether the segment-write error was transient. If a bi-stable segment 15 is successfully updated after a previous failure, an alarm may not be issued. However, if a bi-stable segment 15 is not successfully update after successive writing attempts, the system controller 102 may issue an alarm.

Although FIG. 7 illustrates the bi-stable segment monitoring module 120 as a dedicated circuit module, the functionality of the bi-stable segment monitoring module 120, as well as the level translation module 130, may be incorporated directly into the secondary controller 110 or the display driver 174. In another embodiment, the bi-stable segment monitoring module 120 may be configured to toggle one or more unused bi-stable segments upon each display write command to determine if the display driver 174 is operating correctly.

The bi-stable segment monitoring module 120 may also be operable to monitor a serial data output port of the display driver 174 to determine the status of the display driver 174. The display driver 174 may comprise a serial data output port to daisy-chain two or more display drivers 174 together. A first display driver may receive display instructions from a controller or other source and pass the display instructions through the serial data output port to the input of another display driver. The data provided on the serial data output port may be monitored and verified against the display instructions that were received by the display driver 174 from the system controller 102 (e.g., by use of a checksum or other data verification means). If the data at the serial data output port is corrupted or not the same as the data provided to the display driver 174, the display driver 174 may be malfunctioning and a bi-stable segment malfunction signal may be sent to the system controller 102.

Some embodiments may also a monitor a display driver status signal 134 provided by the display driver 174. Upon receipt of display instructions, the display driver 174 may provide a "busy" signal indicating that it successfully received the display instructions and is currently performing the write operations. Once the display driver 174 is finished writing to the display device 12, it may provide a "write operation completed" signal. The status signal 134 may be a bit or an output of the display driver 174 wherein the busy signal may be indicated by a logic high voltage and the write operation completed signal may be a logic low voltage. The bi-stable segment monitoring module 120 may be configured to suppress the write operation completed signal or bit if it detects a bi-stable segment malfunction so that the system controller 102 does not receive the write operation completed signal. The system controller 102 may be programmed to issue an alarm if it does not receive the write operation completed signal within a certain period of time.

The charge pump monitoring module 128 will now be described. As described above, the charge pump, which may be included in the display driver 174, is operable to provide the one or more charge pump voltages to the bi-stable segment electrodes via the display driver 174 outputs. To effectively change the state of the bi-stable segments 15 of the display device 12, the charge pump voltages should be within a tolerance range of respective valid charge pump voltage levels. The charge pump monitoring module 128 may monitor the charge pump voltages and compare the monitored charge pump voltages with the respective valid charge pump voltage levels. If a monitored charge pump voltage is not within a tolerance range of the valid charge pump voltage, the charge pump monitoring module 128 (or the secondary controller 110) may provide the system controller 102 with a valid charge pump malfunction signal. The system controller 102 may then issue an alarm such as activation of the buzzer or speaker 178.

The charge pump monitoring module 128 may comprise one or more comparators to monitor the one or more charge pump voltages. If a comparator detects that a charge pump voltage is not within a tolerance range, it may provide a signal to the secondary controller 110 that the charge pump is malfunctioning. In another embodiment, the charge pump monitoring module 128 may comprise an analog to digital converter 113 to determine the charge pump voltage level. If the resulting digital representation of the charge pump voltage indicates that the charge pump voltage is not within tolerance, a charge pump malfunction signal may be provided. In this embodiment, the charge pump monitoring module may include a level translation module 130 to scale the charge pump voltage down to within a voltage range that is acceptable to the analog to digital converter 113. Although the charge pump monitoring module 128 is illustrated as an individual module or circuit, in other embodiments the charge pump monitoring module 128 and its functionality may be integrated into the secondary controller 110 or the system controller 102.

Figure 8:
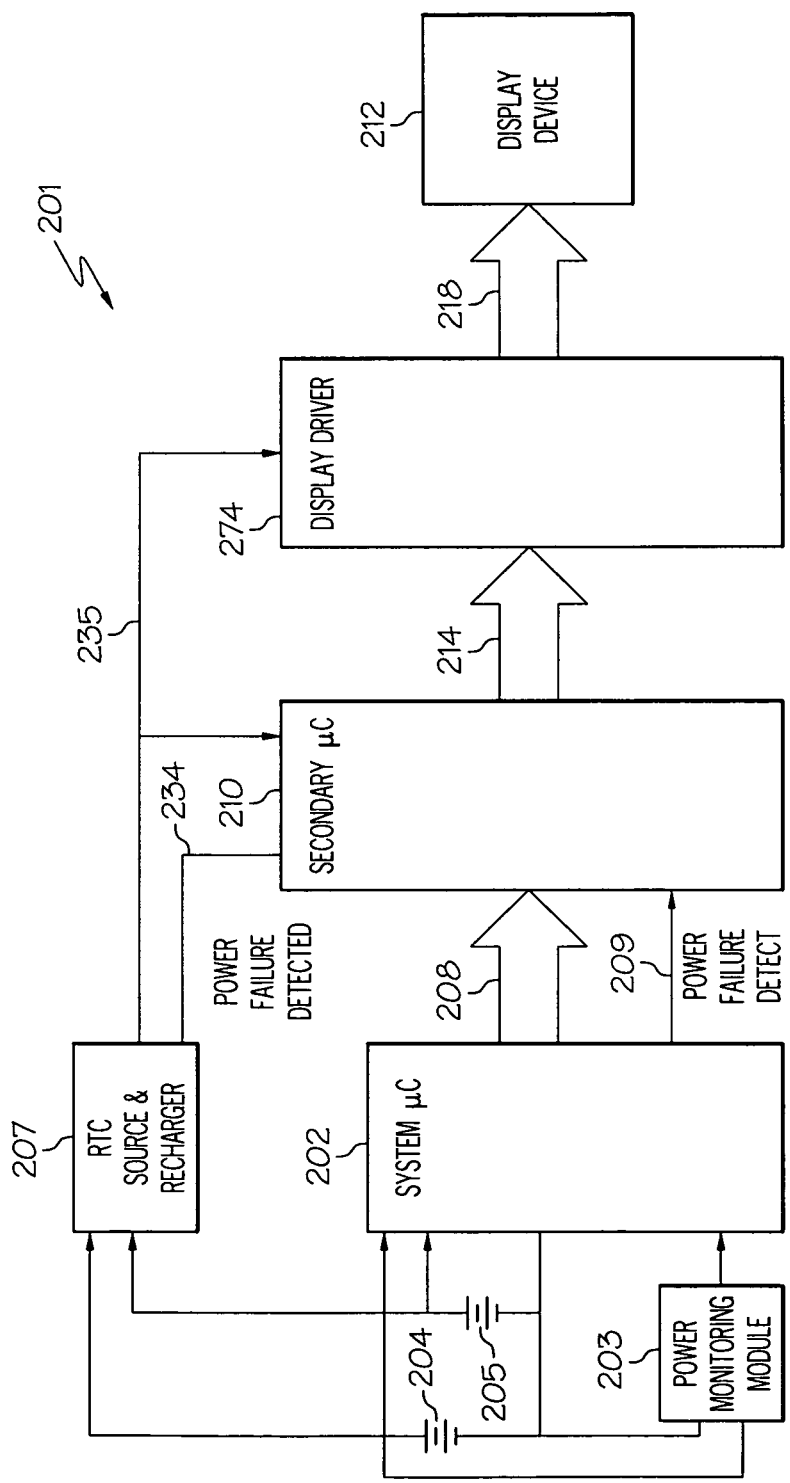
FIG. 8 depicts a schematic diagram of exemplary bi-stable display circuitry for detecting power failure according to one or more embodiments.

Referring now to FIG. 8, exemplary display circuitry 201 for detecting power source failures will now be described. Generally, the display circuitry 201 comprises a secondary controller 210, a display driver 274, a power source monitoring module 203, a primary power source 204, and a secondary power source 205. The primary power source 204, which may be configured as a battery, is configured to provide power to the system controller 202, the secondary controller and the display driver 274. The secondary power source 205 may be a secondary battery or a super capacitor. The secondary power source may be used to operate a real time clock of the system controller 202 when the primary power source 204 is removed.

The power source monitoring module 203 is operable to monitor the output power of the primary power source 204, and may comprise dedicated hardware and/or software. If the output power level, such as a voltage level, drops below a valid power source power value, the power source monitoring module 203 provides a power source alarm signal 209 to the secondary controller 210. The power source monitoring module 203 may be any circuit configured to monitor the power level of the primary power source 204. Operation of the medical diagnostic device 10 under low power conditions may cause unwanted errors such as the inability to write to the display device 212. In the illustrated embodiment, the power source monitoring module 203 provides the system controller 202 with the power source alarm signal 209 which then instructs the secondary controller 210 to write an error message to the display device 212. However, in other embodiments, the power source alarm signal 209 may be provided by the power source monitoring module 203 directly to the secondary controller 210.

Once the secondary controller 210 receives the power source alarm signal 209, it may secure power from the secondary power source 205. The secondary power may be secured via a real time clock source recharger or by switching means that switches the power supply from the primary power source 204 to the secondary power source 205. The secondary controller 210 secures power from the secondary power source 205 for a period long enough to write or clear the display device 12. The display driver 274 may also receive power from the secondary power source 205 or operate using an internal display driver power source.

The secondary controller 210 includes a memory location in which error display data instructions are stored. When the secondary controller 210 receives the power source alarm signal 209, it retrieves the error display data from the memory location and transmits the instructions to the display device 212 as indicated by symbol 214. The display driver 274 then activates outputs in accordance with the error display data (see symbol 218) to update the display device 212. The error display data may instruct the display driver 274 to provide an error message on the display device 212, or to clear the display device 212 of any previous messages so that the display device 212 displays a blank screen. The error message or blank screen may indicate to the user that the medical diagnostic device 10 is malfunctioning and should not be used. After the error message is written to the display device 212, the secondary controller 210 may be configured to disconnect the secondary power source 205 from the circuit to preserve the real time clock function until the primary power source 204 is repaired or replaced.

Referring now to FIG. 9, another embodiment of a bi-stable display fail safe will now be described. As described above, because bi-stable displays may retain a written image without drawing power and are only updated by the application of voltage, a malfunctioning bi-stable segment 15 may mislead the user of a device by providing incorrect information. As an example, if the character 17 of FIG. 9, which may be a most significant digit of a displayed numerical value, is instructed to display a "7," the display driver 74 should provide appropriate voltage levels to the bi-stable segments to cause bi-stable segments A, B and C to turn "on," which may be a black state. However, the display driver 74 may malfunction, or the electrodes of bi-stable segment A may not receive the voltages due to a broken trace, which may cause bi-stable segment A to remain in an "off" state. Therefore, instead of a "7," character 17 would then read as a "1," which may mislead the user of the medical diagnostic device 10. Conversely, if bi-stable segment A fails to turn off and therefore fails in the "on" state, an intended "1" may read as a "7."

Embodiments of the present disclosure may avoid bi-stable segment errors by further segmenting a bi-stable segment 15 into smaller sub-segments 40. Referring to the example above wherein if segment A fails to turn off when displaying a "7," the failure of a sub-segment 40 within main bi-stable segment A would result in a display that may look something like a "7" because only a small portion of bi-stable segment A would be missing. Conversely, if a sub-segment 40 within bi-stable segment A would fail in the on state, the character may display something that may look like a "1." Therefore, a user would not be mislead because the displayed character would still resemble the intended character.

Each of the sub-segments 40 may be electrically coupled to individual outputs of the display driver 74 via conductive traces as described above for the main bi-stable segments 15. The sub-segments 40 may be arranged in close proximity to one another such that any lines separating the sub-segments may be invisible to a user. Some or all of the main bi-stable segments of characters 17 in the display device 12 may be sub-segmented. In one embodiment, only the most critical bi-stable segments 15 may be sub-segmented. For example, bi-stable segment A above may be a considered a critical bi-stable segment 15 because its failure may lead to the display of false information on the display device 12.

Figure 10A:
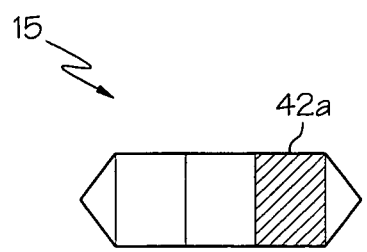
FIG. 10A depicts a sub-segmented bi-stable segment according to one or more embodiments.
Figure 10B:
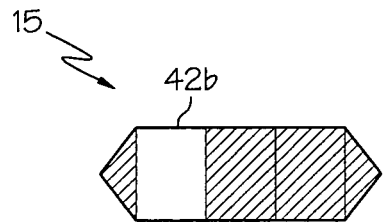
FIG. 10B depicts a sub-segmented bi-stable segment according to one or more embodiments.

Any number of sub-segments may be used. For example, a bi-stable segment 15 comprising five sub-segments is illustrated in FIGS. 10A and 10B. In FIG. 10A, sub-segment 42a has failed in an "on" or dark state while the remaining sub-segments are in the correct "off" or white state. Because the bi-stable segment 15 is sub-segmented, the bi-stable segment 15 still appears to be in a substantially "off" state despite sub-segment 42a being in an "on" state. Similarly, in FIG. 10B, although sub-segment 42b is illustrated as having failed in an "off" state, the bi-stable segment 15 still appears to be in a substantially "on" state.

Figure 11A:
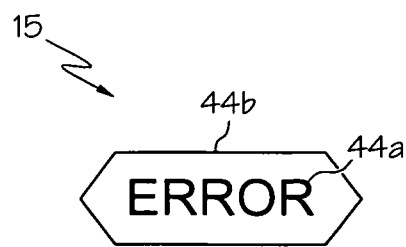
FIG. 11A depicts a sub-segmented bi-stable segment according to one or more embodiments.
Figure 11B:
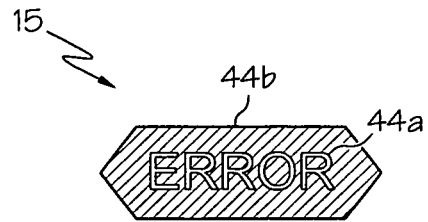
FIG. 11B depicts a sub-segmented bi-stable segment according to one or more embodiments.

Another sub-segment embodiment is illustrated in FIGS. 11A and 11B. A first sub-segment 44a forms the word "ERROR" while a second sub-segment 44b makes up the border of the segment When operating correctly, both sub-segments are in the correct state so that the word ERROR does not appear to the user of the device (i.e., the segment 15 appears all white or all dark). However, if one of the sub-segments 44a, 44b fail, the word ERROR will appear to the user. For example, in FIG. 11A, sub-segment 44b is illustrated in the off state while sub-segment 44a is illustrated in the on state. Therefore, the word ERROR appears as dark text within the segment 15. Conversely, in FIG. 11B, sub-segment 44b is in the on state while sub-segment 44a is in the off state. This causes the word ERROR to appear within the segment 15 as white text. In both cases, the user may be notified that the information that is displayed may contain errors and there may be a problem with the display. The use of the word "ERROR" is only one example as other words or symbols may be utilized.

Embodiments of the present disclosure incorporate a bi-stable display into a device, such as a medical diagnostic device 10. Embodiments may also prevent misleading information from being displayed on the bi-stable display by monitoring bi-stable segment voltage levels, charge pump voltage levels and power levels of a power source. If an error is detected, appropriate action may be taken, such as sounding an alarm, generating an error message or locking out the device. Other embodiments prevent bi-stable display errors by further segmenting main bi-stable segments of a bi-stable character into smaller sub-segments to prevent the failure of an entire bi-stable segment. It will be understood that any of the fail safe techniques described herein may be utilized in conjunction with others in any combination.

It is noted that recitations herein of a component of the present invention being "configured," "programmed" or "operable" in a particular way, "configured," "programmed" or "operable" to embody a particular property, or function in a particular manner, are structural recitations as opposed to recitations of intended use. More specifically, the references herein to the manner in which a component is "configured," "programmed" or "operable" denotes an existing physical condition of the component and, as such, is to be taken as a definite recitation of the structural characteristics of the component.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

What is claimed is:

1. A control circuit for controlling a bi-stable display comprising: a system controller, a display driver, a bi-stable segment monitoring module, and a charge pump, wherein:

the charge pump is configured to generate one or more charge pump voltages;

the bi-stable display comprises a plurality of bi-stable segments capable of transitioning between an on state and an off state with an application of the charge pump voltages;

the display driver comprises a plurality of outputs that correspond to the plurality of bi-stable segments, and is operable to control individual ones of the plurality of bi-stable segments by applying the charge pump voltages to the plurality of bi-stable segments via the plurality of outputs in accordance with display instructions provided by the system controller; and the bi-stable segment monitoring module is operable to detect a bi-stable segment voltage level of at least one output of the display driver and compare the detected bi-stable segment voltage level of the output with a valid bi-stable segment voltage level of the output, wherein:

the display driver is operable to provide a write operation completed signal to the system controller upon successful completion of the display instructions;

the bi-stable segment monitoring module is operable to suppress the write operation completed signal if a detected bi-stable segment voltage level of an output does not equal the valid bi-stable segment voltage level; and the system controller is operable to provide an alarm if the write operation completed signal is not received within a period of time after providing the display instructions to the display driver.

2. The control circuit as claimed in claim 1 further comprising a charge pump monitoring module operable to monitor a charge pump voltage level of the charge pump and compare the monitored charge pump voltage level with a valid charge pump voltage level.

3. The control circuit as claimed in claim 1 wherein the bi-stable segment monitoring module is operable to provide a bi-stable segment malfunction signal to the system controller if the detected bi-stable segment voltage level of the output does not equal the valid bi-stable segment voltage level.

4. The control circuit as claimed in claim 3 wherein the system controller is operable to provide an alarm upon receipt of the bi-stable segment malfunction signal.

5. The control circuit as claimed in claim 1 wherein:
each bi-stable segment of the bi-stable display comprises a top electrode and a bottom electrode;
the top electrode and the bottom electrode are electrically coupled to an output of the display driver;
the bi-stable segment monitoring module is operable to measure a voltage level at the top electrode and the bottom electrode;
the bi-stable segment monitoring module is operable to detect a differential voltage between the voltage level at the top electrode and the voltage level at the bottom electrode; and
the bi-stable segment monitoring module is operable to provide a bi-stable segment malfunction signal to the system controller if the detected differential voltage between the voltage level at the top electrode and the voltage level at the bottom electrode does not equal a valid differential voltage.

6. The control circuit as claimed in claim 1 wherein:
the display driver is configured to provide the display instructions at a serial data output port; and
the bi-stable segment monitoring module is operable to receive the display instructions from the serial data output port, compare the display instructions received at the serial data output port with the display instructions from the system controller, and provide a bi-stable segment malfunction signal to the system controller if the display instructions received at the serial data output port do not equal the display instructions provided by the system controller.

7. The control circuit as claimed in claim 2 wherein the charge pump monitoring module is operable to provide a charge pump malfunction signal to the system controller if the monitored charge pump voltage level is not within a tolerance range of the valid charge pump voltage level.

8. The control circuit as claimed in claim 7 wherein the system controller is operable to provide an alarm upon receipt of the charge pump malfunction signal.

9. The control circuit as claimed in claim 7 wherein the charge pump monitoring module comprises a comparator configured to provide the charge pump malfunction signal to the system controller if the monitored charge pump voltage level is not within a tolerance range of the valid charge pump voltage level.

10. The control circuit as claimed in claim 7 wherein the charge pump monitoring module comprises an analog to digital converter to measure the charge pump voltage level.

11. The control circuit as claimed in claim 2 further comprising a secondary controller, wherein:

the bi-stable segment monitoring module is operable to provide a bi-stable segment malfunction signal to the secondary controller if the detected bi-stable segment voltage level of the output does not equal the valid bi-stable segment voltage level;

the charge pump monitoring module is operable to provide a charge pump malfunction signal to the secondary controller if the monitored charge pump voltage level is not within a tolerance range of the valid charge pump voltage level; and the secondary controller is configured to provide the bi-stable segment malfunction signal and the charge pump malfunction signal to the system controller.

12. The control circuit as claimed in claim 1 wherein:
the control circuit further comprises a primary power source, a secondary controller, and a power source monitoring module;
the primary power source is operable to supply power to the control circuit;
the power source monitoring module is operable to monitor a power level of the primary power source and compare the monitored power level with a valid power source power level; and
the power source monitoring module is further operable to provide a power source alarm signal to the secondary controller if the monitored power level is not within a tolerance range of the valid power source power level.

13. The control circuit as claimed in claim 12 wherein:
the control circuit further comprises a secondary power source;
the secondary controller is operable to secure power from the secondary power source and provide error display data to the display driver upon receipt of the power source alarm signal; and
the display driver is operable to control individual ones of the plurality of bi-stable segments of the bi-stable display in accordance with the error display data.

14. A method for controlling a bi-stable display having a plurality of bi-stable segments each capable of transitioning between an on state and an off state via application of a voltage, comprising:
providing the voltage from a charge pump to a display driver;
supplying the voltage to individual ones of the plurality of bi-stable segments via a plurality of outputs from the display driver in accordance with display instructions provided by a system controller;
detecting both a bi-stable segment voltage level of at least one of the plurality of outputs of the display driver and a charge pump voltage level of the voltage;
comparing both the detected bi-stable segment voltage level with a valid bi-stable segment voltage level and the detected charge pump voltage level with a valid charge pump voltage level;
providing a malfunction signal to the system controller if either the detected bi-stable segment voltage level is not equal to the valid bi-stable segment voltage level, or the charge pump voltage level is not within a tolerance range of the valid charge pump voltage level;
providing a write operation completed signal from the display driver to the system controller upon successful completion of the display instructions;
suppressing the write operation completed signal to the system controller by a bi-stable segment monitoring module if a detected bi-stable segment voltage level of an output does not equal the valid bi-stable segment voltage level; and providing an alarm from the system controller if the write operation completed signal is not received within a period of time after providing the display instructions to the display driver.

15. The method as claimed in claim 14 further comprising monitoring a charge pump voltage level of the charge pump and comparing the monitored charge pump voltage level with a valid charge pump voltage level via a charge pump monitoring module.

16. The method as claimed in claim 14 further comprising providing a bi-stable segment malfunction signal from the bi-stable segment monitoring module to the system controller if the detected bi-stable segment voltage level of the output does not equal the valid bi-stable segment voltage level.

17. The method as claimed in claim 16 further comprising providing an alarm upon receipt by the system controller of the bi-stable segment malfunction signal.

18. The method as claimed in claim 14 further comprising detecting a differential voltage between a voltage level at a top electrode and a voltage level at a bottom electrode of the bi-stable display; and providing a bi-stable segment malfunction signal to the system controller if the detected differential voltage between the voltage level at the top electrode and the voltage level at the bottom electrode does not equal a valid differential voltage.

19. The method as claimed in claim 14 further comprising comparing display instructions received at a serial data output port with the display instructions from the system controller, and providing a bi-stable segment malfunction signal to the system controller if the display instructions received at the serial data output port do not equal the display instructions provided by the system controller.

20. The method as claimed in claim 15 further comprising providing a charge pump malfunction signal to the system controller if the monitored charge pump voltage level is not within a tolerance range of the valid charge pump voltage level.

21. The method as claimed in claim 20 further comprising providing an alarm upon receipt by the system controller of the charge pump malfunction signal.

22. The method as claimed in claim 14 further comprising providing a secondary controller; providing the malfunction signal to the secondary controller if the detected bi-stable segment voltage level of the output does not equal the valid bi-stable segment voltage level; providing a charge pump malfunction signal to the secondary controller if a monitored charge pump voltage level is not within a tolerance range of a valid charge pump voltage level; and providing, via the secondary controller, the bi-stable segment malfunction signal and the charge pump malfunction signal to the system controller.

23. The method as claimed in claim 14 further comprising providing a primary power source, a secondary controller, and a power source monitoring module; supplying power to the control circuit via the primary power source; monitoring, via the power source monitoring module, a power level of the primary power source and comparing the monitored power level with a valid power source power level; and providing, via power source monitoring module, a power source alarm signal to the secondary controller if the monitored power level is not within a tolerance range of the valid power source power level.

24. The method as claimed in claim 23 further comprising providing a secondary power source; providing power from the secondary power source upon receipt by the secondary controller of the power source alarm signal; and providing from the secondary controller error display data to the display driver such that the display driver controls individual ones of the plurality of bi-stable segments of the bi-stable display in accordance with the error display data.

25. A control circuit for controlling a bi-stable display comprising:
a system controller, a display driver, a bi-stable segment monitoring module, and a charge pump, wherein:
the charge pump is configured to generate one or more charge pump voltages;
the bi-stable display comprises a plurality of bi-stable segments capable of transitioning between an on state and an off state with an application of the charge pump voltages;
the display driver comprises a plurality of outputs that correspond to the plurality of bi-stable segments, and is operable to control individual ones of the plurality of bi-stable segments by applying the charge pump voltages to the plurality of bi-stable segments via the plurality of outputs in accordance with display instructions provided by the system controller; and
the bi-stable segment monitoring module is operable to detect a bi-stable segment voltage level of at least one output of the display driver and compare the detected bi-stable segment voltage level of the output with a valid bi-stable segment voltage level of the output, wherein:
each bi-stable segment of the bi-stable display comprises a top electrode and a bottom electrode;
the top electrode and the bottom electrode are electrically coupled to an output of the display driver;
the bi-stable segment monitoring module is operable to measure a voltage level at the top electrode and the bottom electrode;
the bi-stable segment monitoring module is operable to detect a differential voltage between the voltage level at the top electrode and the voltage level at the bottom electrode; and
the bi-stable segment monitoring module is operable to provide a bi-stable segment malfunction signal to the system controller if the detected differential voltage between the voltage level at the top electrode and the voltage level at the bottom electrode does not equal a valid differential voltage.

26. The control circuit as claimed in claim 25 further comprising a charge pump monitoring module operable to monitor a charge pump voltage level of the charge pump and compare the monitored charge pump voltage level with a valid charge pump voltage level.

27. The control circuit as claimed in claim 25 wherein the system controller is operable to provide an alarm upon receipt of the bi-stable segment malfunction signal.

28. The control circuit as claimed in claim 26 wherein the charge pump monitoring module is operable to provide a charge pump malfunction signal to the system controller if the monitored charge pump voltage level is not within a tolerance range of the valid charge pump voltage level.

29. The control circuit as claimed in claim 28 wherein the system controller is operable to provide an alarm upon receipt of the charge pump malfunction signal.

30. The control circuit as claimed in claim 26 wherein the charge pump monitoring module comprises a comparator configured to provide a charge pump malfunction signal to the system controller if the monitored charge pump voltage level is not within a tolerance range of the valid charge pump voltage level.

31. The control circuit as claimed in claim 26 wherein the charge pump monitoring module comprises an analog to digital converter to measure the charge pump voltage level.

32. The control circuit as claimed in claim 26 further comprising a secondary controller, wherein:
the bi-stable segment monitoring module is operable to provide the bi-stable segment malfunction signal to the secondary controller if the detected bi-stable segment voltage level of the output does not equal the valid bi-stable segment voltage level;
the charge pump monitoring module is operable to provide a charge pump malfunction signal to the secondary controller if the monitored charge pump voltage level is not within a tolerance range of the valid charge pump voltage level; and
the secondary controller is configured to provide the bi-stable segment malfunction signal and the charge pump malfunction signal to the system controller.

33. The control circuit as claimed in claim 25 wherein:
the control circuit further comprises a primary power source, a secondary controller, and a power source monitoring module;
the primary power source is operable to supply power to the control circuit;
the power source monitoring module is operable to monitor a power level of the primary power source and compare the monitored power level with a valid power source power level; and
the power source monitoring module is further operable to provide a power source alarm signal to the secondary controller if the monitored power level is not within a tolerance range of the valid power source power level.

34. The control circuit as claimed in claim 33 wherein:
the control circuit further comprises a secondary power source;
the secondary controller is operable to provide power from the secondary power source and provide error display data to the display driver upon receipt of the power source alarm signal; and
the display driver is operable to control individual ones of the plurality of bi-stable segments of the bi-stable display in accordance with the error display data.

35. A control circuit for controlling a bi-stable display comprising: a system controller, a display driver, a bi-stable segment monitoring module, and a charge pump, wherein:
the charge pump is configured to generate one or more charge pump voltages;
the bi-stable display comprises a plurality of bi-stable segments capable of transitioning between an on state and an off state with an application of the charge pump voltages;
the display driver comprises a plurality of outputs that correspond to the plurality of bi-stable segments, and is operable to control individual ones of the plurality of bi-stable segments by applying the charge pump voltages to the plurality of bi-stable segments via the plurality of outputs in accordance with display instructions provided by the system controller; and
the bi-stable segment monitoring module is operable to detect a bi-stable segment voltage level of at least one output of the display driver and compare the detected bi-stable segment voltage level of the output with a valid bi-stable segment voltage level of the output, wherein:
the display driver is configured to provide the display instructions at a serial data output port; and
the bi-stable segment monitoring module is operable to receive the display instructions from the serial data output port, compare the display instructions received at the serial data output port with the display instructions from the system controller, and provide a bi-stable segment malfunction signal to the system controller if the display instructions received at the serial data output port do not equal the display instructions provided by the system controller.

36. The control circuit as claimed in claim 35 further comprising a charge pump monitoring module operable to monitor a charge pump voltage level of the charge pump and compare the monitored charge pump voltage level with a valid charge pump voltage level.

37. The control circuit as claimed in claim 35 wherein the bi-stable segment monitoring module is operable to provide the bi-stable segment malfunction signal to the system controller if the detected bi-stable segment voltage level of the output does not equal the valid bi-stable segment voltage level.

38. The control circuit as claimed in claim 37 wherein the system controller is operable to provide an alarm upon receipt of the bi-stable segment malfunction signal.

39. The control circuit as claimed in claim 36 wherein the charge pump monitoring module is operable to provide a charge pump malfunction signal to the system controller if the monitored charge pump voltage level is not within a tolerance range of the valid charge pump voltage level.

40. The control circuit as claimed in claim 39 wherein the system controller is operable to provide an alarm upon receipt of the charge pump malfunction signal.

41. The control circuit as claimed in claim 36 wherein the charge pump monitoring module comprises a comparator configured to provide a charge pump malfunction signal to the system controller if the monitored charge pump voltage level is not within a tolerance range of the valid charge pump voltage level.

42. The control circuit as claimed in claim 36 wherein the charge pump monitoring module comprises an analog to digital converter to measure the charge pump voltage level.

43. The control circuit as claimed in claim 36 further comprising a secondary controller, wherein:
the bi-stable segment monitoring module is operable to provide the bi-stable segment malfunction signal to the secondary controller if the detected bi-stable segment voltage level of the output does not equal the valid bi-stable segment voltage level;
the charge pump monitoring module is operable to provide a charge pump malfunction signal to the secondary controller if the monitored charge pump voltage level is not within a tolerance range of the valid charge pump voltage level; and
the secondary controller is configured to provide the bi-stable segment malfunction signal and the charge pump malfunction signal to the system controller.

44. The control circuit as claimed in claim 35 wherein:
the control circuit further comprises a primary power source, a secondary controller, and a power source monitoring module;
the primary power source is operable to supply power to the control circuit;
the power source monitoring module is operable to monitor a power level of the primary power source and compare the monitored power level with a valid power source power level; and
the power source monitoring module is further operable to provide a power source alarm signal to the secondary controller if the monitored power level is not within a tolerance range of the valid power source power level.

45. The control circuit as claimed in claim 44 wherein:
the control circuit further comprises a secondary power source;
the secondary controller is operable to provide power from the secondary power source and provide error display data to the display driver upon receipt of the power source alarm signal; and
the display driver is operable to control individual ones of the plurality of bi-stable segments of the bi-stable display in accordance with the error display data.

* * * * *

UNITED STATES PATENT AND TRADEMARK OFFICE
CERTIFICATE OF CORRECTION

PATENT NO. : 8,436,844 B2
APPLICATION NO. : 12/486805
DATED : May 7, 2013
INVENTOR(S) : Paul S. Rutkowski et al.

It is certified that error appears in the above-identified patent and that said Letters Patent is hereby corrected as shown below:

In the Specification

Col. 2, Line 27, ", and is operable apply" should read --, and is operable to apply--;

Col. 8, Line 33, "b-stable" should read --bi-stable--;

Col. 8, Line 62, "is not successfully update" should read --is not successfully updated--;

Col. 9, Line 23, "may also a monitor a" should read --may also monitor a--;

Col. 11, Line 45, "may be a considered a" should read --may be considered a--; and Col. 11, Line 61, "segment" should read --segment.--.

Signed and Sealed this
Twenty-fourth Day of December, 2013

Margaret A. Focarino
*Commissioner for Patents of the United States Patent and Trademark Office*